United States Patent [19]

Biard et al.

[11] Patent Number: 5,096,920
[45] Date of Patent: Mar. 17, 1992

[54] 1,2-DITHIOL-3-THION-S-OXIDE COMPOUNDS AND PHARMACEUTICAL COMPOSITIONS

[75] Inventors: Dominique Biard, Trivier sur Moignans; Marie-Odile Christen, Paris; Patrick Dansette, Paris; Daniel Jasserand, Paris; Daniel Mansuy, Paris, all of France; Amor Sassi, Beni Hassan par Monastir, Tunisia

[73] Assignee: Kali-Chemie Pharma GmbH, Hanover, Fed. Rep. of Germany

[21] Appl. No.: 357,271

[22] Filed: May 26, 1989

[30] Foreign Application Priority Data

May 27, 1988 [EP] European Pat. Off. ........ 88401304.6

[51] Int. Cl.$^5$ .................. A61K 31/385; C07D 339/02
[52] U.S. Cl. .................................. 514/441; 514/838; 514/893; 514/894; 549/37
[58] Field of Search ................ 549/36, 37; 514/441, 514/838, 893, 894

[56] References Cited

U.S. PATENT DOCUMENTS

| | | | |
|---|---|---|---|
| 2,556,963 | 6/1951 | Gaudin | 568/75 |
| 2,662,899 | 12/1953 | Bashour | 549/36 |
| 2,688,620 | 9/1954 | Gaudin | 549/36 |
| 2,816,116 | 12/1957 | Fields | 549/36 |
| 3,214,442 | 10/1965 | Klingsberg | 549/37 |
| 3,225,062 | 12/1965 | Klingsberg | 549/37 |
| 3,847,943 | 11/1974 | Warner | 549/37 |

FOREIGN PATENT DOCUMENTS 874447 4/1953 Fed. Rep. of Germany ........ 549/37

OTHER PUBLICATIONS

Voronkov et al., "The Reaction of Sulfur with Organic Compounds", *Chem. of Het. Compdls, 4 vol. 1 #3 (1965)* p. 224.

Baehring-Kuhlmey, "Anethole Trithione", Chem. Abs., 89:117589c (1978).

Nuhrich et al., "Heterocyclic Sulfur Antifungal Compounds . . . ," Chem. Abs., 105:168761j (1986).

Behringer, Hans, "Preparation and π-Electronic Structure of 1,2-Dithiole-3-Thione Oxides", Chem. Abs., 96:162569b (1982).

Perez et al., "3H-1,2-Dithiol-3-Thion-S-Oxide", *Liebigs Ann. Chem.* 1981, pp. 1510-1512.

Tamagaki et al., "Sulfines in the Oxidations of 1,2-Dithiole-3-Thiones", *Chemistry Letters*, 1980, pp. 619-620.

Behringer et al., "Darstellung und πElektronen-Struktur . . . ", *Phosphorus and Sulfur*, vol. 12, (1981) pp. 115-122.

"Empfehlungen der Deutschen Gesellschaft fur Klinische Chemie", *Z. klin. Chem. u. klin. Biochem.*, vol. 8 (1970), pp. 658-60.

"Recommendations of the German Society for Clinical Chemistry", *Z. Klin. Chem. Klin. Biochem.*, vol 10 (1972), pp. 281-291.

Pedersen et al., "Studies on Organophosphorus Compounds-XXVIII", *Tetrahedron*, vol. 35 (1979), pp. 2433-2437.

*Primary Examiner*—C. Warren Ivy
*Assistant Examiner*—Catherine S. Kilby Scalzo
*Attorney, Agent, or Firm*—Foley & Lardner

[57] ABSTRACT

The use of 5-phenyl-3H-1,2-dithiol-3-thion-S-oxides which are optionally substituted in the phenyl ring as active substances in hepato-protective medicaments and new 5-phenyl-3H-1,2-dithiol-3-thion-S-oxides which are substituted in the phenyl ring are described.

8 Claims, No Drawings

1,2-DITHIOL-3-THION-S-OXIDE COMPOUNDS AND PHARMACEUTICAL COMPOSITIONS

BACKGROUND OF THE INVENTION

The present invention relates to the use of 5-phenyl-1,2-dithiol-3-thion-S-oxide compounds as active pharmacological substances, in particular for the treatment and prophylaxis of liver damage in larger mammals, in particular humans, and medicaments which contain 5-phenyl-1,2-dithiol-3-thion-S-oxide compounds as active substances, and also new 1,2-dithiol-3-thion-S-oxide compounds having valuable pharmaceutical properties, in particular hepatoprotective properties.

5-Phenyl-3H-1,2-dithiol-3-thion-S-oxide is known from studies on oxidation reactions of trithiones by Perez et al, (Liebigs Ann. Chem. 1981, 1512), Tamayaki et al (Chem. Lett. 1980, 619–620) and Behringer et al (Phosphorus and Sulfur, 12, (1981), 115–122). However, no pharmacological activity has hitherto been described for this compound.

Anetholtrithione (=5-(4-methoxyphenyl)-3H-1,2-dithiol-3-thione is a medicament which is commercially available as a choleretic (commercial products Sulfarlem ®, Felvitin ®), and of which it is known that it also possesses hepato-protective properties.

SUMMARY OF THE INVENTION

The object of the present invention is to develop new medicaments for prophylaxis and treatment of liver damage. In addition, the object of the invention is to produce new 1,2-dithiol-3-thione derivatives with valuable pharmacological properties.

It has now been found that the 1,2-dithiol-3-thion-S-oxide compounds of general Formula I,

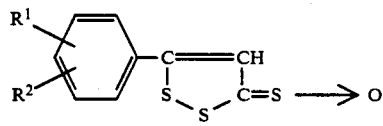

wherein
$R^1$ is hydrogen, alkyl with 1–4 carbon atoms, lower alkoxy, hydroxy, halogen, trifluoromethyl or nitro, and
$R^2$ is hydrogen, halogen or lower alkoxy, or
$R^1$ and $R^2$ are bonded to adjacent carbon atoms and together form alkylene dioxy with 1–2 carbon atoms, possess valuable pharmacological properties and in particular exhibit hepato-protective properties.

They are characterized in particular by effects which protect the liver from damaging effects of exogenous hepato-toxic substances and have good compatibility and low toxicity.

Due to their pharmacological properties, in particular their hepato-protective effects, the 1,2-dithiol-3-thion-S-oxide compounds of Formula I are suitable as medicaments, in particular for prophylaxis and treatment of liver damage, for instance liver damage caused by hepato-toxic doses of medicaments, chemical poisons or irradiation.

DETAILED DESCRIPTION OF THE PREFERRED EMBODIMENTS

The lower alkyl groups contained in the groups $R^1$ and $R^2$ of the compounds of Formula I may be straight or branched and preferably contain 1–4, in particular 1–2, carbon atoms. Lower alkoxy groups $R^1$ or $R^2$ may contain 1–4 carbon atoms, and in particular represent methoxy. Fluorine, chlorine or bromine, preferably chlorine or fluorine, are suitable as halogen substituents $R^1$ or $R^2$.

If $R^1$ is an alkyl group, it preferably represents methyl and is preferably arranged in the 2 or 3 position. Halogen substituents $R^1$ are preferably arranged in the 4 position. Preferably, $R^2$ is hydrogen.

The 5-phenyl-1,2-dithiol-3-thion-S-oxide compounds of Formula I have valuable pharmacological properties, in particular hepato-protective properties, and are characterized by good compatibility and low toxicity.

Thus the substances have the ability to protect the liver from damaging effects, e.g. liver damage occurring after taking hepatotoxic exogenous substances, or to counteract such effects.

It is known that a range of chemical substances and also of medicaments can cause damage to liver cells at suitably high doses and can lead to hepatic cytolysis and liver necrosis. In the case of cytolytic liver damage, an increased release of some transaminases from the damaged liver cells into the blood stream occurs. In the case of liver damage, therefore, the blood level values of these transaminases are increased, and by measuring the serum activity of these transaminases it is possible to determine liver damage and assess the extent thereof.

A known substance which has a liver-damaging effect is e.g. acetaminophen [=Paracetamol =4-(N-acetylamino)-phenol], which is in general use as an analgesic in physiologically acceptable doses, but which is a strongly hepato-toxic substance in high doses. High doses of acetaminophen also lead to liver damage in rodents which is comparable to human liver necrosis. Acetaminophen is therefore used as a standard hepatotoxic substance in standard pharmacological tests on animals in order to evaluate the hepato-protective properties of test substances.

The compounds of Formula I have a marked protective action against the liver-damaging effects of acetaminophen, as can be shown in the standard pharmacological tests on animals described below.

The metabolism and the hepato-toxic effect of acetaminophen have been described in depth in the literature. For instance, it is known that conjugation of acetaminophen metabolites to glutathione plays a major part in the detoxification and elimination of acetaminophen, and that its hepato-toxic effects occur particularly strongly if there is a deficiency of glutathione in the cell, caused, for instance, by excessive dosing. Furthermore, it is known that the hepato-toxicity is partly caused by covalent bonding of a metabolically formed reactive agent to macro-molecules of the hepatic tissue, and that peroxidation of lipids of the cell membrane and the over-production of reactive radicals, inter alia, oxygen radicals, caused thereby plays a key part in the hepato-toxicity of acetaminophen. The hepato-protective effects of 5-phenyl-1,2-dithiol-3-thion-S-oxide compounds of Formula I with respect to acetaminophen-induced damage can therefore be regarded as an indication that the compounds have lipid peroxidation-inhibiting properties and may act anti-oxidatively and as a radical binder.

DESCRIPTION OF THE PHARMACOLOGICAL TESTS (A) Determination of the protective action with respect to the mortality in mice caused by an overdose of acetaminophen For the tests, groups of 20 or 30 female mice in each case, having a body weight of approximately 20 g, were used. During the tests, the animals were given a daily food ration, and had available an unlimited supply of water with a pH of 3.

The animals were intoxicated by i.p. application of 1000 mg/kg acetaminophen suspended in 0.5 ml of an aqueous gum arabic solution.

One hour before intoxication, the animals of a test group were given 50 mg/kg per os of the test substance as a suspension, applied with a stomach tube. A control group with the same number of animals was given only the suspending agent one hour before intoxication.

The number of animals in each test group which had died in a period of 6 days was determined and the protective action of the substance was calculated in % protection obtained (=difference in the number of animals which had died in the test group from the number of animals which had died in the respective control group, divided by the number of animals per group).

Table A below reproduces the results obtained according to the test method described above. The example numbers given for the compounds of Formula I relate to the production examples below.

TABLE A

| Example No. | Protective action against acetaminophen-induced lethality in mice Number of dead animals/total number of animals per test group | % dead animals | Δ % protection achieved |
|---|---|---|---|
| 11 | 1/20 | 5 | 94.6 |
| 12 | 4/20 | 20 | 78.4 |
| 4 | 1/20 | 5 | 94.6 |
| 14 | 2/20 | 10 | 89.2 |
| 6 | 3/30 | 10 | 89.2 |
| 7 | 6/30 | 20 | 78.4 |
| 8 | 14/30 | 47.6 | 49.6 |
| 9 | 3/30 | 10 | 89.2 |
| 1 | 3/30 | 10 | 89.2 |
| 5 | 9/30 | 30 | 67.6 |
| Control animal groups | 648/700 | 92.6 | |

(B) Determination f the protective action with respect to the liver damage in mice which is induced by acetaminophen and which leads to an increase in the transaminase values in the serum For the tests, female mice having a body weight of approximately 25 g were used. The animals were given a food ration, and had available an unlimited supply of water with a pH of 3.

The animals were intoxicated by i.p. application of 450 acetaminophen suspended in 0.5 ml of aqueous gum arabic solution.

One hour before intoxication, as a preventive measure, a first group of test animals were given 75 mg/kg per os of the test substance as a suspension, applied with a stomach tube. A second group of control animals was only given the suspending agent one hour before intoxication.

18 Hours after the application of acetaminophen, the animals were killed and drained of blood by severing the carotid artery.

Blood samples from 2 animals in each case were poured into a test tube together, allowed to stand at room temperature for 2-3 hours, decanted for one hour at 4° C. and then centrifuged for 10 min. at 2,500 × g.

The supernatant serum was transferred into plastic test tubes, and the activities of the transaminases SGOT (=Serum Glutamate-Oxalacetate Transaminase) and SGPT (=Serum Glutamate-Pyruvate Transaminase) in international units/1/min were determined therein according to known standard methods under the optimized standardization conditions recommended by the German Society for Clinical Chemistry (see Z. klin. Chem. u. klin. Biochem. 8 (1970), 658-660 and ibid 10 (1972), 281-283). The activities were measured at a wavelength of 334 nm using an automated spectrophotometer (spectrophotometer No. 61, manufactured by the Eppendorff Company) and a reagent kit for GOT and GPT determination produced by Boehringer-Mannheim (=automatic GOT and GPT kit opt., Diagnostics No. 258 822 and 258 784 produced by Boehringer-Mannheim GmbH).

The results obtained by the test method described above are reproduced in Table B. In the table, the transaminase activities are given in international units/1/min. For the control animal groups which had not received prior treatment and for the test animal groups which had received prior treatment, in each case the mean values (=m) for the group which were formed from the individual results and the standard deviations (=sem) are given. Furthermore, the protective action in % protection achieved (=difference between the mean serum activity values of the control group and of the test animal group which had received prior treatment, divided by the mean value of the control animal group) was calculated and given.

TABLE B

| Example No. | Acetaminophen-induced transaminase activity in control animal groups not previously treated | | | Acetaminophen-induced transaminase activity in previously-treated test animal groups | | | % protection against acetaminophen induced transaminase activity | |
|---|---|---|---|---|---|---|---|---|
| | Number of animals per group | Activity in international units/1/ min. (m +/− sem) | | Number of animals per group | Activity in international units/1/ min. (m +/− sem) | | | |
| | | SGOT | SGPT | | SGOT | SGPT | SGOT | SGPT |
| 9 | 46 | 1811 ± 330 | 2170 ± 434 | 17 | 200 ± 14.5 | 57.7 ± 3 | 88.4 | 97.3 |
| 11 | 64 | 1826 ± 255 | 2362 ± 348 | 16 | 210 ± 5 | 70 ± 4 | 88.5 | 97.0 |
| 12 | 63 | 1563 ± 224 | 1611 ± 220 | 16 | 205 ± 8 | 58 ± 3 | 86.9 | 96.4 |
| 14 | 64 | 1914 ± 239 | 2192 ± 441 | 16 | 230 ± 12 | 58 ± 5 | 88.0 | 97.3 |
| 4 | 64 | 1914 ± 239 | 2192 ± 441 | 16 | 171 ± 6 | 46 ± 4 | 91.1 | 97.9 |
| 1 | 46 | 1811 ± 330 | 2170 ± 434 | 18 | 205 ± 8 | 69 ± 6 | 89.7 | 96.8 |

TABLE B-continued

| Example 6 No. | Acetaminophen-induced transaminase activity in control animal groups not previously treated | | | Acetaminophen-induced transaminase activity in previously-treated test animal groups | | | % protection against acetaminophen induced transaminase activity | |
|---|---|---|---|---|---|---|---|---|
| | Number of animals per group | Activity in international units/1/ min. (m +/− sem) | | Number of animals per group | Activity in international units/1/ min. (m +/− sem) | | | |
| | | SGOT | SGPT | | SGOT | SGPT | SGOT | SGPT |
| 5 | 54 | 1413 ± 203 | 1414 ± 343 | 16 | 185 ± 10 | 53.5 ± 4 | 88.9 | 96.2 |
| 13 | 63 | 1563 ± 224 | 1611 ± 220 | 16 | 204 ± 2 | 64 ± 3 | 87.0 | 96.1 |
| 6 | 62 | 2924 ± 273 | 3586 ± 331 | 16 | 258 ± 16 | 85 ± 3 | 91.2 | 97.6 |
| 7 | 62 | 2924 ± 273 | 3586 ± 331 | 16 | 322 ± 16 | 78 ± 3 | 89.0 | 97.8 |

Due to their pharmacological properties, in particular their hepato-protective effects; the compounds of Formula I are suitable for prophylaxis and treatment of liver damage. For instance, the substances are suitable for the prophylaxis and treatment of pathological conditions which are connected with liver damage, e.g. cirrhoses of the liver, unintentional or accidental intoxication with hepatotoxic chemicals, e.g. herbicides, hepatotoxic overdoses of medicaments, treatment with medicaments having hepatotoxic side-effects, e.g. in cancer chemotherapy, hepato-toxic radiation damage, e.g. in cancer radiation therapy.

The doses to be used may differ individually and naturally vary according to the type of condition to be treated, the substance used and the form of administration. In general, however, medicinal forms with an active substance content of 5-50 mg per single dose are suitable for application to larger mammals, particularly humans.

The invention also relates to new 1,2-dithiol-3-thion-S-oxide compounds of the general Formula Ia,

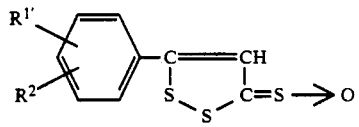

wherein
$R^1$ is alkyl with 1-2 carbon atoms, lower alkoxy, hydroxy, halogen, trifluoromethyl or nitro, and
$R^2$ is hydrogen, halogen or lower alkoxy, or
$R^{1'}$ and $R^2$ are bonded to adjacent carbon atoms and together form alkylene dioxy with 1-2 carbon atoms, and their production.

1,2-Dithiol-3-thion-S-oxide compounds of the general Formula I may be obtained by oxidizing in a known way corresponding 1,2-dithiol-3-thione compounds of the general Formula II,

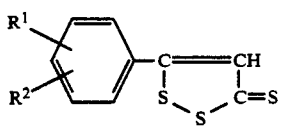

wherein $R^1$ and $R^2$ have the above meanings.

The oxidation of the compounds of Formula II to form the corresponding compounds of Formula I may be carried out according to known methods for the oxidation of 1,2-dithiol-3-thiones to form the corresponding S-oxides, for instance the methods described in the works cited above.

The literature sources cited above give, as suitable oxidation agents, for instance, hydrogen peroxide in the presence of an organic solvent containing hydroxy groups, for instance acetic acid or methanol; peracetic acid in an aromatic hydrocarbon such as benzene; 3-chloroperbenzoic acid in an aprotic solvent which is inert under the reaction conditions, for instance a halogenated hydrocarbon such as dichloromethane or chloroform or also acetone; or sodium periodide in a mixture of acetone and a lower alcohol, in particular methanol. The oxidation agents are advantageously used in approximately equivalent quantities, preferably not more than 20% excess, and the reaction is stopped as soon as no more starting material is detectable in the reaction mixture. The reaction temperature may vary depending on the type of oxidation agent used, and may be, for instance, between −10° C. and 50° C. If desired, further organic solvents, which are inert under the reaction conditions, for instance aromatic hydrocarbons, such as benzene or toluene, may be added to the reaction medium. Oxidation by means of approximately equivalent quantities (up to 15% excess) of 3-chloroperbenzoic acid at low temperature, for instance temperatures between −23° C. and room temperature, has proved particularly favorable.

The resulting compounds of Formula I may be isolated form the reaction mixture and purified in a known manner.

The 5-phenyl-3H-1,2-dithiol-3-thione compounds of Formula II which are used as starting products are known and/or may be produced according to known method or analogously to known methods.

For instance, in order to produce compounds of Formula IIb,

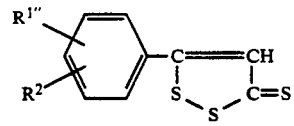

wherein $R^{1''}$ has the meaning given for $R^1$ with the exception of hydroxy and $R^2$ has the above meaning, Ketoesters of the general Formula III,

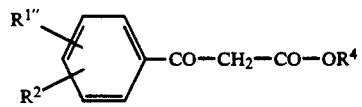

wherein $R^{1''}$ and $R^2$ have the above meanings $R^4$ is lower alkyl, in particular ethyl, are cyclicsingly sulfurated in a known manner, for instance by treatment with $P_4S_{10}$, or particularly advantageously according to the method described by Pedersen and Lawesson (cf. Tetrahedron 35, 2433-2437) by reacting with 2,4-bis(4- methoxyphenyl)-1,3-dithia-2,4-diphosphetan-2,4-disulfide of Formula IV,

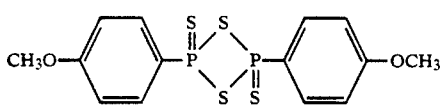

(=known as Lawesson's reagent), preferably in the presence of elemental sulfur. The reaction with Lawesson's reagent and elemental sulfur takes place in a solvent which is inert under the reaction conditions, for instance an anhydrous aromatic hydrocarbon such as toluene at high temperature, desirably the boiling temperature of the reaction mixture. Advantageously, 1-2 moles of the compound of Formula IV and 1-2 moles of elemental sulfur are used per 1 mole of the ketoester of Formula III.

Compounds of Formula II may also be obtained by reacting olefin compounds of Formula V,

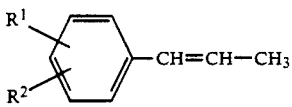

wherein $R^1$ and $R^2$ have the above meanings, with sulfur at high temperature in an organic solvent. The reaction is preferably carried out at high temperature, for instance, temperatures of 175-235° C., using sulfolane as a solvent according to the method described in U.S. Pat. No. 3,847,943.

Compounds of Formula IIb may also be obtained starting from acetophenone compounds of Formula VI,

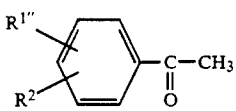

wherein $R^{1''}$ and $R^2$ have the above meanings, by first condensing them in the presence of a base with carbon disulfide into compounds of formula VII,

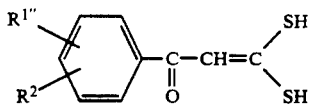

wherein $R^{1''}$ and $R^2$ have the above meanings, and further reacting these intermediate products with phosphorus pentasulfide to form compounds of Formula II.

The reaction of compounds of Formula VI with carbon disulphide may be carried out, for example, according to the method described by Thuillier et al (cf. Bull. Soc. Chim. France, serie 5, Memoires presentes a la Soc. Chim. (1959), 1398-1401). Thus, the reaction suitably takes place in an inert organic solvent, e.g. benzene or ether, using a tertiary alkaline metal alcoholate, e.g. sodium butylate or sodium amylate. The reaction of the intermediate products obtained thereby with $P_2S_5$ suitably takes place in an aromatic hydrocarbon such as toluene or xylene at the boiling temperature of the reaction mixture.

In order to produce compounds of Formula II, wherein $R^1$ is hydroxy, corresponding compounds of Formula II, wherein $R^1$ is methoxy, can be demethylated in a known manner. For instance, the methoxy group may be cleaved acidicly by treating with pyridinium chloride.

The compounds of Formula I may be contained according to the invention together with conventional pharmaceutical auxiliaries and/or carriers in solid or liquid pharmaceutical preparations. Examples of solid preparations include preparations which can be administered orally, such as capsules, tablets, granulates or coated pills, or also suppositories. Solid preparations may contain conventional pharmaceutical inorganic and/or organic carriers such as talcum, lactose or starch as well as conventional pharmaceutical auxiliaries or adjuvants, for instance lubricants such as magnesium stearate or tablet disintegrating agents. Suppositories may contain known suppository bases. Liquid preparations such as solutions, suspensions or emulsions may contain the usual diluents, e.g. water, or paraffins, and/or dispersing agents such as polyethylene glycols and the like. In addition, other auxiliaries or adjuvants may be added, such as preservatives, stabilizing agents, masking flavors and the like.

The active substances may be mixed and formulated with the pharmaceutical auxiliaries and/or carriers in a known way. In order to produce solid medicinal forms, the active substances may, for instance, be mixed with the auxiliaries and/or carriers in a conventional manner and be granulated in the wet or dry state. Depending on the type of adjuvants used, optionally a powder which can be directly made into tablets may also be obtained by simple mixing. The granulate or powder may be filled directly into capsules or may be pressed into tablet cores in a conventional manner. These may be made into coated pills in a known manner, if desired.

The following examples illustrate explain the invention, but are not intended to limit its scope in any way.

EXAMPLE 1

5-(4-chlorophenyl)-1,2-dithiol-3-thion-S-oxide (a) 22.7 g (=0.1 Mol) of 4-chlorobenzoyl ethyl acetate, 100 g (=0.25 Mol) Lawesson's reagent (=2,4-bis(4-methoxyphenyl) -1,3-dithia-2,4-diphosphetan-2,4-disulfide) and 6.4 g (=0.2 Mol) elemental sulfur were stirred in 100 ml anhydrous toluene for 10 hours at 100° C. For working up, the reaction mixture containing the resulting 5-(4-chlorophenyl)-1,2-dithiol-3-thione was cooled to room temperature, filtered, and the filtrate was poured onto a 300 g silica gel column. The toluene was eluted with light petroleum ether, and then the 5-(4-chlorophenyl)-1,2-dithiol-3-thione was eluted with a toluene/light petroleum ether mixture (50 : 50). The resulting crude product was purified for a second time over a silica gel column using toluene/light petroleum ether as an eluant, and re-crystallized from toluene. 9.6 g of 5-(4-chlorophenyl)-1,2-dithiol-3-thione with a melting point of 135° C. were obtained.

(b) 4.9 g (=0.02 Mol) of 5-(4-chlorophenyl)-1,2-dithiol-3-thione were dissolved in 60 ml chloroform. The solution was cooled to 03C, and a solution of 5.3 g 80-90% pure 3-chloroperbenzoic acid (approximately 0.026 Mol) in 150 ml chloroform was added in drops to the cooled solution. After the addition, which lasted about 30 minutes, had ended, the red-colored reaction mixture was kept for a further hour at 0° C.

For working up, the reaction mixture was first washed with 100 ml aqueous saturated sodium bicarbonate solution and then with water, and dried over sodium sulfate and filtered. The filtered solution was reduced to about 30 ml at room temperature under reduced pressure, poured onto a 175 g silica gel column and eluted with chloroform. Non-reacted starting material was hereby first separated off and thus could be recovered, and subsequently the 5-(4-chlorophenyl)-1,2-dithiol-3-thion-S-oxide formed during oxidation was obtained. The eluate fractions containing the S-oxide were evaporated at room temperature under reduced pressure. The remaining residue was crystallized by the addition of light petroleum ether. The 5-(4-chlorophenyl)-1,2-dithiol-3-thion-S-oxide which was obtained as a red solid was filtered off and quickly dried in air. 3.4 g of the S-oxide with a melting point of 123-125° C. were obtained.

EXAMPLE 2

5-(4-hydroxyphenyl)-1,2-dithiol-3-thion-S-oxide (a) A mixture of 100 g (=0.41 Mol) of 5-(4-methoxyphenyl)-1,2-dithiol-3-thione and 335 g (=2.9 Mol) of pyridinium chloride were heated to a temperature of 210-215° C. for 4 hours. Thereafter, the reaction mixture was allowed to cool to 80° C. and was then washed with 2 l warm water in order to remove the pyridinium salt. 400 ml 10% aqueous sodium hydroxide solution were added to the residue. The resulting sodium salt of the resulting 5-(4-hydroxyphenyl)-1,2-dithiol-3-thione was filtered off, dissolved in 500 ml warm water, and the 5-(4-hydroxyphenyl)-1,2-dithiol-3-thione was precipitated by adding acetic acid. The precipitate was filtered-off under suction and dried. The resulting crude product was dissolved in a warm mixture of 300 ml ethanol and 25 ml diethylamine, and the solution was poured onto a short aluminum oxide column. The column was eluted with 100 ml warm ethanol. The resulting red eluate solution was evaporated to half its volume under reduced pressure. The diethylamine salt of the 5-(4-hydroxyphenyl)-1,2-dithiol-3-thione thereby crystallized out. The red crystals were filtered off and poured into 250 ml dilute hydrochloric acid. The suspension which resulted thereby was stirred for one hour at room temperature. Then the 5-(4-hydroxyphenyl)-1,2-dithiol-thione which was separated off as a solid precipitate was filtered-off, washed with water and dried over phosphorus pentoxide 23.5 g of 5-(4-hydroxyphenyl)-1,2-dithiol-3-thione with a melting point of 192° C. were obtained.

(b) A solution of 9.4 g 80-90% pure 3-chloroperbenzoic acid (=approximately 0.046 Mol) in 200 ml acetone was added dropwise with vigorous stirring to a solution of 10 g (=0.004 Mol) 5-(4-hydroxyphenyl)-1,2-dithiol-3-thione in 300 ml acetone within one hour at room temperature. Thereafter, the reaction mixture was kept at the same temperature for a further hour. The 5-(4-hydroxyphenyl)-1,2-dithiol-3-thion-S-oxide which resulted as a red precipitate was filtered-off under suction and dried over phosphorus pentoxide. 9.4 g of the S-oxide with a melting point of 118-124° C. were obtained.

The compounds of Formula I listed in the following Table may also be produced according to the method described in the foregoing Examples by oxidation of corresponding compounds of Formula II.

TABLE 1

| Example No. | $R^1$ | $R^2$ | Melting point in °C. |
|---|---|---|---|
| 3 | 4-OC$_2$H$_5$ | H | D |
| 4 | H | H | 110 |
| 5 | 2-Cl | 4-Cl | 129-131 |
| 6 | 2-OCH$_3$ | H | 103-104 |
| 7 | 2-F | H | 85 |
| 8 | 2-Cl | H | 82 |
| 9 | 4-OCH$_3$ | H | 91-93 |
| 10 | 2-NO$_2$ | 4-Cl | 108-109 |
| 11 | 3-OCH$_3$ | H | 120-122(D) |
| 12 | 2-OC$_2$H$_5$ | H | D |
| 13 | 4-CH$_3$ | H | 97 |
| 14 | 4-F | H | 97 |
| 15 | 3-CF$_3$ | H | 95-96 |
| 16 | 3-Br | 4-OCH$_3$ | 107-110 |
| 17 | 4-OH | 3-OCH$_3$ | 184-185 |
| 18 | 3-OH | H | 182 |
| 19 | 3,4-O—CH$_2$—O | | 162 |
| 20 | 2-CH$_3$ | H | 102-104 |

D = Decomposition

EXAMPLE I

Tablets containing 5-(4-chlorophenyl)-3H-1,2-dithiol-3-thion-S-oxide

Tablets with the following composition per tablet are produced:

| | |
|---|---|
| 5-(4-chlorophenyl)-3H-1,2-dithiol-3-thion-S-oxide | 15 mg |
| Corn starch | 65 mg |
| Lactose | 135 mg |
| Gelatine (as 10% solution) | 6 mg |

The active substance, the corn starch and the lactose are bodied with the 10% gelatine solution. The paste is ground and the resulting granules are placed on a suitable tray and dried at 453° C. The dried granules are passed through a crusher and mixed in a mixer with the following additional auxiliaries:

| | |
|---|---|
| Talcum | 5 mg |
| Magnesium stearate | 5 mg |
| Corn starch | 9 mg |
| and then pressed into 240 mg tablets. | |

EXAMPLE II

Capsules containing 5-phenyl-3H-1,2-dithiol-3-thion-S-oxide.

Capsules with the following composition per capsule are produced:

| | |
|---|---|
| 5-phenyl-3H-1,2-dithiol-3-thion-S-oxide | 10 mg |
| Lactose | 65 mg |
| Corn starch | 40 mg |
| Soluble starch | 4 mg |
| Magnesium stearate | 1 mg |

The active substance is mixed with lactose and corn starch. The resulting mixture is thoroughly moistened with a 15% aqueous solution of the soluble starch and granulated. The moist material is passed through a 1.6 mm sieve, dried at 40° C. and then passed through a 1.0 mm sieve. After mixing the granules with magnesium stearate, the resulting mixture is poured into capsules in quantities of 120 mg.

Capsules are also produced according to the method described in Example II which contain 5-(2-methoxyphenyl)-3H-1,2-dithiol-3-thion-S-oxide or 5-(4-fluorophenyl)-3H-1,2-dithiol-3-thion-S-oxide as the active substance.

The foregoing description and examples have been set forth merely to illustrate preferred embodiments of the invention and are not intended to be limiting. Since modifications of the described embodiments incorporating the spirit and substance of the invention may occur to persons skilled in the art, the scope of the invention should be limited solely with reference to the appended claims and equivalents thereof.

What is claimed is:

1. A 1,2-dithiol-3-thion-S-oxide compound corresponding to the Formula Ia:

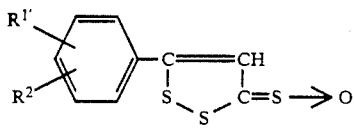

wherein $R^{1'}$ represents alkyl with 1-4 carbon atoms, lower alkoxy, hydroxy, halogen, trifluoromethyl or nitro, and $R^2$ represents hydrogen, halogen or lower alkoxy, or $R^{1'}$ and $R^2$ are bonded to adjacent carbon atoms and together form an alkylene dioxy group with 1-2 carbon atoms.

2. A compound according to claim 1, wherein $R^{1'}$ is selected from the group consisting of fluorine, chlorine and methoxy, and $R^2$ is hydrogen.

3. A method of inhibiting liver damage in a mammal comprising administering to said mammal an effective hepato-protective amount of a compound corresponding to the Formula I:

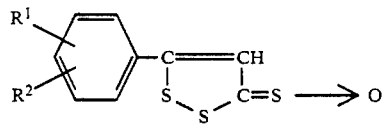

wherein $R^1$ represents hydrogen, alkyl with 1-4 carbon atoms, lower alkoxy, hydroxy, halogen, trifluoromethyl or nitro, and $R^2$ represents hydrogen, halogen or lower alkoxy, or $R^1$ and $R^2$ are bonded to adjacent carbon atoms and together form an alkylene dioxy group with 1-2 carbon atoms.

4. A method according to claim 3, wherein $R^1$ represents alkyl with 1-4 carbon atoms, lower alkoxy, hydroxy, halogen, trifluoromethyl or nitro.

5. A method according to claim 3, wherein $R^1$ is selected from the group consisting of hydrogen, fluorine, chlorine and methoxy, and $R^2$ is hydrogen.

6. A pharmaceutical composition comprising an effective hepato-protective amount of a compound corresponding to the Formula I:

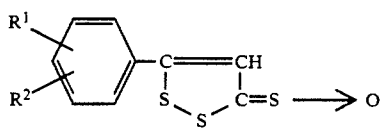

wherein $R^1$ represents hydrogen, alkyl with 1-4 carbon atoms, lower alkoxy, hydroxy, halogen, trifluoromethyl or nitro, and $R^2$ represents hydrogen, halogen or lower alkoxy, or $R^1$ and $R^2$ are bonded to adjacent carbon atoms and together form an alkylene dioxy group with 1-2 carbon atoms, and a conventional pharmaceutical carrier or adjuvant.

7. A pharmaceutical composition according to claim 6, wherein $R^1$ represents alkyl with 1-4 carbon atoms, lower alkoxy, hydroxy, halogen, trifluoromethyl or nitro.

8. A pharmaceutical composition according to claim 6, wherein $R^1$ is selected from the group consisting of hydrogen, fluorine, chlorine and methoxy, and $R^2$ is hydrogen.

* * * * *